United States Patent [19]

Casagrande et al.

[11] Patent Number: 5,025,011
[45] Date of Patent: Jun. 18, 1991

[54] FUSED PYRIDINES ACTIVE ON THE CARDIOVASCULAR SYSTEM

[75] Inventors: Cesare Casagrande, Arese; Stefania Montanari; Francesco Santangelo, both of Milan, all of Italy

[73] Assignee: SIMES, Societa Italiana Medicinali e Sintetici S.p.A., Vicenza, Italy

[21] Appl. No.: 390,018

[22] Filed: Jul. 25, 1989

[30] Foreign Application Priority Data

Jul. 29, 1988 [IT] Italy .................. 21544 A/88

[51] Int. Cl.$^5$ ............... A61K 31/435; A61K 31/495; A61K 31/50; C07D 471/04
[52] U.S. Cl. ......................... 514/234.2; 514/234.5; 514/248; 514/258; 514/300; 544/117; 544/127; 544/236; 544/279; 546/113; 546/123
[58] Field of Search ............ 544/236, 117; 514/248, 514/234.2

[56] References Cited

U.S. PATENT DOCUMENTS

| | | | |
|---|---|---|---|
| 4,134,980 | 1/1979 | Eberlein et al. | 514/248 |
| 4,145,432 | 3/1979 | Sato | 544/236 |
| 4,223,142 | 9/1980 | Denzel et al. | 544/236 |
| 4,438,128 | 3/1984 | Wiedemann et al. | 514/248 |

FOREIGN PATENT DOCUMENTS

| | | |
|---|---|---|
| 0133530 | 2/1985 | European Pat. Off. |
| 0180833 | 5/1986 | European Pat. Off. |
| 0189898 | 8/1986 | European Pat. Off. |
| 0194752 | 9/1986 | European Pat. Off. |
| 8604581 | 8/1986 | World Int. Prop. O. |

OTHER PUBLICATIONS

Kleinschroth et al., Chemical Abstracts, vol. 105, No. 72685 (1986) (Abstract for DE 3438350 or EP 180833).
Sostanze Farmaceutiche by Kleeman & Engel, pp. 1, 115, 169, 198, 264, 269, 285, 296, 298, 311, 337, 365, 960, 1012, 1079, 1130, 1142, 1181, 1213, 1299, 1313, 1346, 1444, 1504, 1606, 1607, 1635, 1718 (1988).
Chemical Abstracts, Sato et al, 88:170127f, p. 592, 1978.

Primary Examiner—Diana Rivers
Assistant Examiner—E. Bernhardt
Attorney, Agent, or Firm—Irwin M. Aisenberg

[57] ABSTRACT

Compounds of the formula

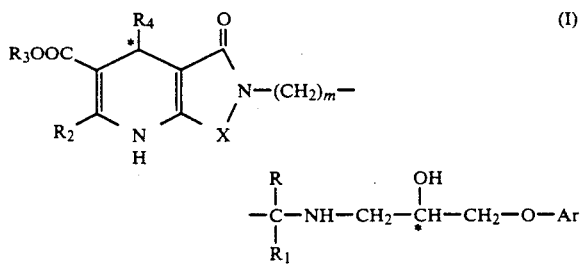

(wherein Ar, R, $R_1$, $R_2$, $R_3$, $R_4$, X and m have the meanings given in the description), their preparation and pharmaceutical compositions containing them.

The compounds of formula I are active on the cardiovascular system as antivasospastics, antiangina pectoris agents, antihypertensives and vasodilators.

4 Claims, No Drawings

FUSED PYRIDINES ACTIVE ON THE CARDIOVASCULAR SYSTEM

The present invention relates to compounds active on the cardiovascular system; more particularly, it relates to bicyclic compounds having a dihydropyridine nucleus, pharmaceutically acceptable salts thereof, processes for preparing them and pharmaceutical compositions containing them. Compounds having calcium-antagonist properties and a bicyclic structure are known. Examples of such known compounds are the 4-oxo-pyrido(2,3-d)pyrimidines described in European Patent Application No. 180833, the 1,6-naphthyridinones described in the European Patent Applications No. 133530 and No. 189898, all in the name of Godecke Aktiengesellschaft, or in U.S. Pat. No. 4,304,914 (USV Pharmaceutical Corp.), the 5-oxo-1,7-naphthiridines described in U.S. Pat. Nos. 4,596,873 and 4,321,384 (American Home Products Corp.) and the pyrrole-pyridines described in Japanese Patent Application No. 52/153995 (Sankyo K.K.).

Beta-blocking drugs are also known and widely used in therapy for treating cardiovascular diseases; in most cases these drugs are structurally related to 3-aryloxy-2-hydroxypropanamine.

Examples of the beta-blockers most commonly used in therapy, mainly as antihypertensives, are Alprenolol (Merck Index, X ed., No. 304), Atenolol (Merck Index, X ed., No. 868), Carteolol (Merck Index, X ed., No. 1850), Metoprolol (Merck Index, X ed., No. 6027), Madolol (Merck Index, X ed., No. 6195), Oxprenol (Merck Index, X ed., No. 6820), Pindolol (Merck Index, X ed., No. 7317), Propanolol (Merck Index, X ed., No. 7740), and Timolol (Merck Index, X ed., No. 9284).

Now we have found a novel class of compounds wherein both a typical beta-blocker structure and a calcium-antagonist moiety are suitably interconnected.

It is an object of this invention to provide a compound of the formula:

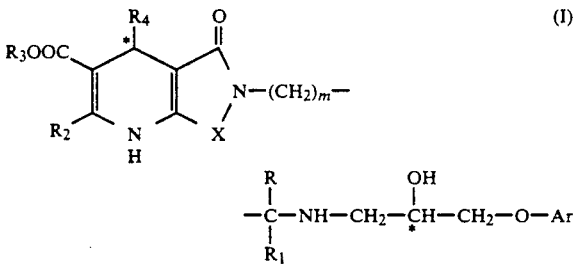

wherein
Ar is a mono- or di-cyclic aromatic or heteroaromatic ring system, optionally substituted by one or more substituents selected from halogen, hydroxy, $C_1$–$C_5$ alkyl, $C_3$–$C_6$ cycloalkyl, $C_2$–$C_5$ alkenyl, $C_1$–$C_3$ alkoxy, alkoxyalkyl having from 1 to 5 carbon atoms both in the alkyl and in the alkoxy moiety and an optional unsaturation in the chain, phenoxy, phenylalkoxy, aminocarbonylalkyl having from 1 to 3 carbon atoms in the alkyl moiety, cyano, alkoxycarbonyl, alkylcarbamoyl, amino, mono- and di-alkylamino, pyrrolidinyl, piperidino and morpholino;

R and $R_1$, the same or different, are hydrogen or $C_1$–$C_3$ alkyl;

$R_2$ is cyano, amino or $C_1$–$C_3$ alkyl group optionally substituted by fluorine.

$R_3$ is $C_1$–$C_6$ alkyl optionally substituted by a group selected from hydroxy, alkoxy, amino, mono- and di-alkylamino, pyrrolidinyl, piperidino and morpholino;

$R_4$ is a ring selected from phenyl, naphthyl, tetrahydronaphthyl, indanyl wherein said ring may be substituted by one or more substituents selected from halogen, hydroxy, $C_1$–$C_5$ alkyl, $C_2$–$C_5$ alkenyl, $C_1$–$C_3$ alkoxy, $C_2$–$C_5$ alkenyloxy, alkoxyalkyl having from 1 to 5 carbon atoms both in the alkyl and alkoxy moiety, $C_2$–$C_5$ alkanoyl, trifluoromethyl, amino, nitro, carbamoyl, cyano, $C_1$–$C_3$ alkylthio, carbamoyl($C_1$–$C_6$)alkyl and $C_1$–$C_6$ alkanoylamino.

X is $CH_2$ or a saturated or unsaturated aliphatic chain having 2 members wherein at least one member is a carbon atom and the other member is a nitrogen atom or a carbon atom;

m is 1, 2 or 3;

and salts thereof with organic or inorganic pharmaceutically acceptable acids.

The compounds of formula I have at least two asymmetric carbon atoms and can therefore exist as stereoisomers.

Another object of this invention is to provide the compounds of formula I both as a stereoisomeric mixture and as single stereoisomers.

The single stereoisomers are obtained by stereoselective synthesis or by separation from the sterosiomeric mixture according to known techniques as fractional crystallization, chromatography and resolution by means of salification or preparation of derivatives with optically active compounds.

The salts of the compounds of the present invention with organic and inorganic pharmaceutically acceptable acids are prepared according to known methods.

Examples of pharmaceutically acceptable acids according to this invention are hydrochloric, hydrobromic, phosphoric, sulphuric, lactic, succinic, tartaric, acetic, salicylic, citric, benzoic, p-hydroxybenzoic, naphthalene-2-sulfonic, adipic and pimelic acid.

The compounds of formula I and their pharmaceutically acceptable acid addition salts are active on the cardiovascular system as antivasospastics, antiangina agents, antihypertensives and vasodilators.

Preferred compounds of formula I are represented by the following formulas

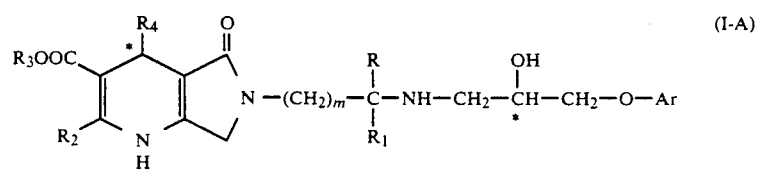

-continued

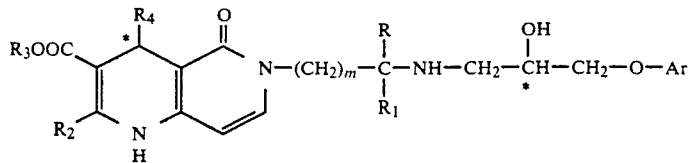
(I-B)

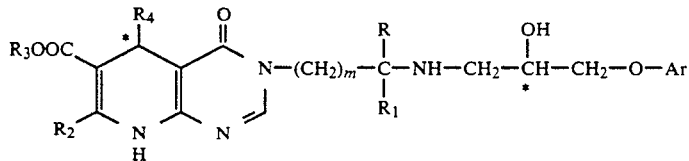
(I-C)

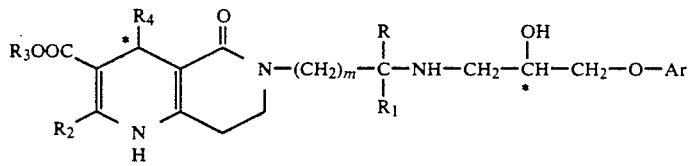
(I-D)

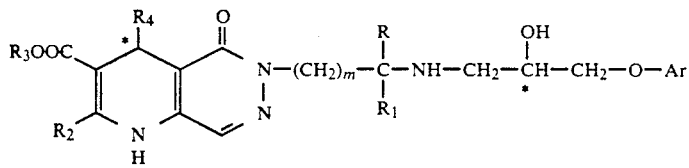
(I-E)

wherein Ar, R, $R_1$, $R_2$, $R_3$, $R_4$ and m have the meanings given for formula I.

Preferred meanings of Ar are phenyl, naphthyl, isobenzofuranyl, benzofuranyl, 3,4-dihydro-carbostyryl, benzopyranyl tetrahydronaphthyl, carbazolyl, indenyl, indolyl, 1,2,5-thiadiazolyl, optionally substituted.

Examples of possible substituents comprise one or more fluorine, chlorine, bromine, acetyl, allyl, carbamoylmethyl, butyroylamino, cyclohexyl, cyano, hydroxy, butyroyl, acetylamino, methoxycarbonyl, methoxyethyl, methoxy, allyloxy, cyclopentyl, cyclopropyl, morpholino, ethyl and isobutyroyl.

Specific examples of substituted aryls are 2-methoxyphenyl, 2-allyloxyphenyl, 2-cyanophenyl, 2-methylphenyl, 2-allylphenyl, 4-carbamoylmethylphenyl, 4-hydroxyphenyl, 4-morpholino-1,2,5-thiadiazol-3-yl, indol-4-yl, and 3,4-dihydro-1-(H)-carbostyryl-5-yl.

Even more preferred compounds of formula I are those wherein R and $R_1$, which may be the same or different, are hydrogen or methyl; $R_2$ is methyl; $R_3$ is methyl, ethyl or isopropyl; $R_4$ is phenyl optionally substituted and m is 1.

A further object of the present invention is to provide a method for preparing a compound of formula I which comprises a)(i) condensing a compound of the formula

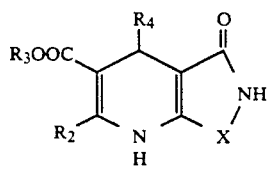
(II)

wherein $R_2$, $R_3$, $R_4$ and X have the above cited meanings, with a protected amine of the formula

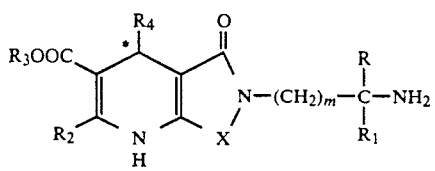
(III)

wherein R, $R_1$ and m have the above cited meanings and W is a leaving group; in an inert solvent and at a temperature of from room temperature to the reflux temperature of the reaction mixture, optionally in the presence of an organic or inorganic base, and (ii) removing the protective group to obtain a compound of the formula

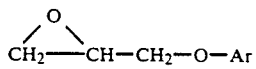
(IV)

wherein R, $R_1$, $R_2$, $R_3$, $R_4$, X and m have the above mentioned meanings, and (iii) reacting the (IV) with an epoxide of the formula

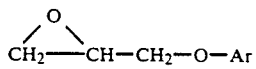
(V)

or with a chlorohydrin of the formula

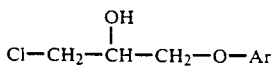
(VI)

wherein Ar has the above mentioned meaning; in an inert solvent at a temperature of from room temperature to the reflux temperature of the reaction mixture to obtain a compound of the formula I; or b)(i) condensing an aldehyde of formula

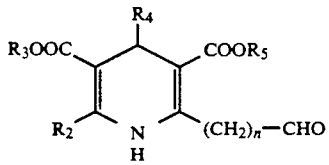

wherein $R_2$, $R_3$ and $R_4$ have the above mentioned meaning; $R_5$ is $C_1$-$C_3$ alkyl and 0 is 0 or 1; with an optionally protected diamine of the formula

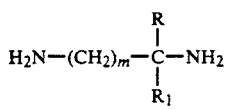

wherein R, $R_1$ and m have the above mentioned meanings; in the presence of a dehydrating agent or by azeotropic removal of the water formed in the course of the reaction to afford an imino intermediate which, by subsequent reaction with a reducing agent, cyclization with elimination of alcohol ($R_5OH$) and removal, of the possible protective group, fields compounds of the formula

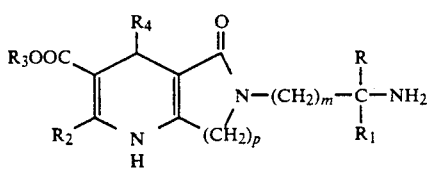

wherein R, $R_1$, $R_2$, $R_3$, $R_4$ and m have the above mentioned meanings and p is 1 or 2; and (ii) reacting the compound of formula IV-A with an epoxide V or a chlorohydrin VI, as mentioned in step (a)(iii) above, to afford a compound of formula I-A (p=1) or I-D (p=2); or c) alkylating an optionally protected amine of formula VIII with a dihydropyridine of the formula

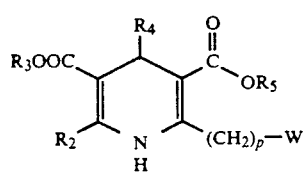

wherein R, $R_2$, $R_3$, $R_4$, $R_5$ and W have the above mentioned meanings; to give a compound of the formula

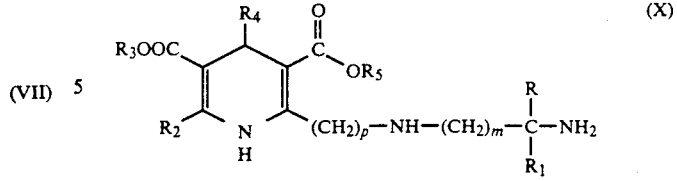

wherein R, $R_1$, $R_2$, $R_3$, $R_4$, $R_5$ m and p have the above mentioned meanings; heating the compound of formula (X) to give a compound of formula (IV-A) with concurrent elimination of alcohol ($R_5OH$), and subsequent treatment of compound (IV-A) according to point b above; or d) condensing an aldehyde of formula VII (n=0) with an amino alkyl hydrazine of the formula

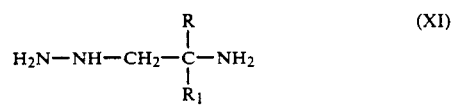

wherein R and $R_1$ have the above mentioned meanings; to obtain the amino intermediate of the formula

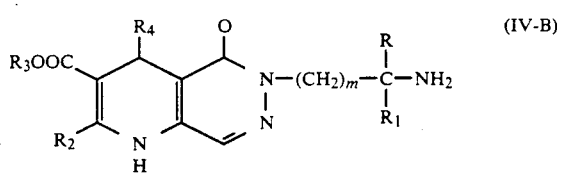

wherein R, $R_1$, $R_2$, $R_3$, $R_4$ and m have the above mentioned meanings: which is then reacted with an epoxide V or a chlorohydrin VI, according to step (a)(iii) above, to afford a compound of formula I-E; or e) cyclizing a compound of the formula

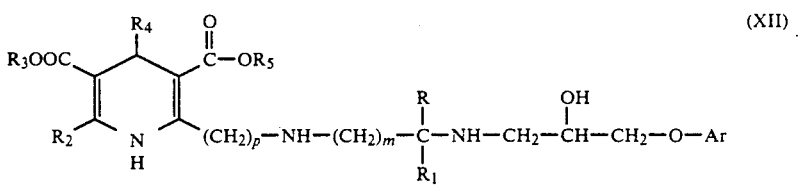

wherein R, $R_1$, $R_2$, $R_3$, $R_4$, $R_5$, Ar m and p have the above mentioned meanings; to afford a compound of formula I-A and I-D.

Examples of suitable protective groups used in connection with the compounds of formula (III) and (VIII) are benzyloxycarbonyl, benzyl and t.butyloxycarbonyl; a suitable protection is also afforded when the nitrogen atom becomes a part of an imido ring, such as phthalimido.

Examples of preferred meanings of W in the compound of formula (III) and (IX) are iodine, mesyl and tosyl.

Examples of suitable bases in step (a)(i) above are the inorganic bases, such as alkali and alkaline-earth metals hydroxides and carbonates, preferably sodium and potassium hydroxides and carbonates, and the organic bases, such as triethylamine and pyridine; these bases being used in excess to the compound of formula (II). Alternatively the step is performed in the presence of a strong base, such as sodium hydride, sodium methylate and sodium amide.

Examples of suitable solvents in step (a)(i) above are ethers, such as dioxane and dimethoxyethane; aliphatic and aromatic hydrocarbons, such as petroleum ether, toluene and xylene; and amides, such as dimethylformamide.

The removal of the protective group in step (a)(ii) above is preferably carried out by hydrogenolysis, acid hydrolysis or by treatment with hydrazine or methylamine.

Examples of preferred inert solvents in step (a)(iii) are the alcohols and the hydrocarbons; typical examples of preferred inert solvents are methyl and ethyl alcohol, and toluene.

Examples of preferred reducing agents in step (b)(i) above are sodium boron hydride and sodium cyano boron hydride.

The preparation of the compounds of formula IV-A in step (c) above may occur in one step without isolation of the intermediate (X) when the alkylation reaction is performed at a temperature promoting the cyclization.

The preparation of the compounds of formula XII can be performed from the corresponding N-triphenyl-methyl-derivatives, disclosed in copending Italian Patent Application No. 21541 A/88 entitled "Compounds active on the cardiovascular system" filed on the same date, via the removal of the protective group according to conventional methods.

The intermediates of formulae II, III, IV, IV-A, IV-B, V, VI, VII, VIII, IX, X, XI are known or can be easily prepared according to conventional techniques.

In particular, the compounds of formula II can be prepared according to the methods disclosed in European Patent Applications No. 133530 and No. 180833 (Godecke Aktiengesellschaft) or in Belgian Patent No. 843576 (Fujisawa Pharmaceutical Co.); the compounds of formula IV can be prepared in a way similar to that described in the above mentioned European Patent Application No. 180833; the compounds of formula VIII and IX can be prepared as disclosed in Belgian Patent No. 843576 and in European Patent Application No. 212340 (Boehringer Biochemia Robin S.p.A.), respectively; the compounds of formula X can be prepared according to the method disclosed in European Patent Application No. 225175 (Fisons) and finally the amino alkyl hydrazines XI can be prepared in a way similar to that disclosed by Trepanier et al. in the "Journal of Medicinal Chemistry" 10, 228, (1967).

The preparation of the compounds of formula I as single stereoisomers may be carried out according to conventional separation methods, such as chromatography, crystallization or optical resolution.

Alternatively, it will be evident to the man skilled in the art that it is possible to obtain a compound of formula I having the desired configuration from an intermediate compound of predetermined configuration according to the above described synthesis method.

The compounds of formula I are useful as antivasospastics, antiangina agents, antihypertensives and vasodilators in the treatment of cardiovascular pathologies.

The compounds of formula I proved to be endowed with a remarkable calcium-antagonist and beta-blocking action (example 12) and are useful in producing antihypertensive effects with concomitant reduction of heart rate, contrary to known calcium-antangonists in which the hypotensive effect is accompanied by tachycardia.

A still further object of the present invention is to provide pharmaceutical compositions containing the compounds of formula I or pharmaceutically acceptable salts thereof, optionally together with one or more solid or liquid, organic or inorganic pharmaceutical excipients, such as diluents, preservatives, humectants, dyes, flavours, etc.

The pharmaceutical compositions of the present invention may be administered as solid dosage forms, such as tablets, pills, capsules, granules and suppositories, or as liquid dosage forms, such as syrups, suspensions, emulsions and solutions suitable for oral or parenteral administration.

The compounds of the present invention may also be compounded in slow releasing dosage forms.

The preparation of the pharmaceutical compositions of the present invention is carried out according to usual techniques.

The doses of the compound of formula I to be administered will vary according to several factors, such as the specific activity of the single compound of formula I, the therapy and the individual patient response as well as the selected administration route.

Generally, the amount of the compound of formula I to be administered will be from 0.1 mg to 200 mg per day in one or more repeated doses. For the purpose of better illustrating the present invention, the following examples are now given.

The most characteristic signals of $^1$H-NMR spectra are given.

EXAMPLE 1

Preparation of ethyl 1,4-dihydro-6-methyl-2-(N-(2-(2-hydroxy-3-(2-methoxyphenyoxy)-propylamino)2-methylpropyl)-aminomethyl-4-(3-nitrophenyl)-3,5-pyridinedicarboxylate A mixture of ethyl 1,4-dihydro-2-formyl-6-methyl-4-(3-nitro-phenyl)-3,5-pyridinedicarboxylate (5.04 g; 13 mmoles), and of 2-(2-hydroxy-3-(2-methoxyphenoxy)-propylamino)-2-methylpropylamine (3.47 g; 13 mmoles) in 95% ethanol (70 ml) is stirred for one hour at room temperature.

After having cooled the solution at 0°-5° C., water (6 ml), acetic acid (2.5 ml), sodium acetate (0.65 g) and finally sodium boron hydride (0.49 g; 13 mmoles) are added. Stirring is continued for one hour at room temperature.

The mixture is acidified with dilute hydrochloric acid, evaporated to dryness, taken up with dilute ammonia and extracted with methylene chloride.

After drying over sodium sulfate and evaporation of the solvent, the residue is purified by chromatography on a silica gel column (230-400 mesh) eluting with a mixture of methylene chloride and ethanol (98:2).

Ethyl 1,4-dihydro-6-methyl-2-(N-(2-(2-hydroxy-3-(2-methoxyphenoxy)-propylamino)-2-methylpropyl)-aminomethyl)-4-(3-nitrophenyl)-3,5-pyridinedicarboxylate is thus obtained as a chromatographically pure oil (thin layer chromatography; eluent, methylene chloride:methanol:$NH_4OH$ = 94.5:5:0.5).

$^1$H-NMR (300 MHz, $CDCl_3$): delta (ppm) 1.18-1.33 (12H, m); 2.35 (3H, 2s); 3.85 (3H, s); 4.00 (2H, m); 4.35 (1H, m); 5.05 (1H, 2s); 7.35 (1H, 2t); 7.60 (1H, bd); 8.00 (1H, bd); 8.10 (1H, bs).

EXAMPLE 2

Preparation of ethyl 2methyl-4-(3-nitrophenyl)-5-oxo-6-(2-(2-hydroxy-3-(2-methoxyphenoxy)-propylamino)-2-methylpropyl)-1,4,5,7, tetrahydropyrrol(3,4-b)-pyridine-3-carboxylate hydrochloride A solution of ethyl 1,4-dihydro-6-methyl-2-(N-(2-(2-hydroxy-3-(2-methoxyphenoxy)-propylamino)-2-methylpropyl)-aminomethyl)-4-(3-nitrophenyl)-3,5-pyridinecarboxylate (6.4 g; 10 mmoles), prepared according to example 1, in propanol (50 ml) is refluxed for eight hours.

After evaporation of the solvent, the crude product is purified by chromatography on a silica gel column (230–400 mesh) eluting with a mixture of methylene chloride and ethanol 9:1.

The thus obtained product is treated with a solution of ethyl ether saturated with hydrochloric acid to precipitate ethyl 2-methyl-4-(3-nitrophenyl)-5-oxo-6-(2-(2-hydroxy-3-(2-methoxyphenoxy)-propylamino)-2-methylpropyl)-1,4,5,7-tetrahydropyrrol(3,4-b)pyridine-3-carboxylate hydrochloride.

$^1$H-NMR free base (300 MHz, CDCl$_3$): delta (ppm) 1.10 (9H, m); 2.38 (3H, d); 2.90 (2H, m); 3.02 (1H, dd) 3.48 (1H, dd); 3.84 (3H, s); 5.04 (1H, d); 7.40 (1H, t); 7.72 (1H, m); 8.00 (1H, dd); 8.08 (1H, bs).

EXAMPLE 3

Preparation of methyl 1,4-dihydro-6-methyl-4-(3nitrophenyl)-2-(2-oxo-ethyl)-3,5-pyridinedicarboxylate A solution of methyl 1,4-dihydro-2,6-dimethyl-4-(3-nitrophenyl)-3,5-pyridinedicarboxylate (34.6 g; 0.10 mmoles) and N,N-dimethylformamide dimethyl acetate (14.7; 0.12 mmoles) in dimethylformamide are heated to reflux under a nitrogen atmosphere for 16 hours.

The solvent is evaporated and the crude product is extracted with toluene and water. The organic phase is separated, dryed over sodium sulfate and the solvent is evaporated.

Methyl 1,4-dihydro-2-(2-(N,N-dimethylamino)-ethenyl)-6-methyl-4-(3-nitrophenyl)-3,5-pyridinecarboxylate is obtained and is hydrolyzed without further purification.

A solution of this compound (6g; 15 mmoles) in acetone (60 ml) is treated with hydrochloric acid 6N (6.96 ml) for one hour under nitrogen atmosphere and at room temperature.

The cool solution is evaporated and some water is added, the solution is filtered, the filtrate is diluted with water and extracted with methylene chloride.

After drying over sodium sulfate and evaporation of the solvent, methyl 1,4-dihydro-6-methyl-4-(3-nitrophenyl)-2-(2-oxo-ethyl)-3,5-pyridinedicarboxylate is obtained as a chromatographically pure oil (thin layer chromatography; eluent, methylene chloride :methanol:NH$_4$OH=94.5:5:0.5).

Mass spectrum (chemical ionization, positive ions, isobutane) m/e 374 (M+1)$^+$.

EXAMPLE 4

Preparation of methyl 1,4-dihydro-6-methyl-2-(N-2-(2-hydoxy-3-(2-methoxyphenoxy)-propylamino)-2-methylpropyl)-aminoethyl)-4-(3nitrophenyl)-3,5-pyridinedicarboxylate Operating in a way similar to that described in example 1 but using methyl 1,4-dihydro-6-methyl-4-(3-nitrophenyl)-2-(2-oxo-ethyl)-3,5-pyridinedicarboxylate as starting aldehyde and carrying out the reduction step in dioxane for 16 hours, methyl 1,4-dihydro-6-methyl-2-(N-(2-(2-hydroxy-3-(2-methoxyphenoxy)-propylamino)2-methylpropyl)-aminoethyl)-4-(3-nitrophenyl)-3,5-pyridinedicarboxylate is obtained.

$^1$H-NMR (300 MHz, CDCl$_3$): delta (ppm): 1.30 (6H, s); 2.42 (3H, 2s); 3.61 (3H, s); 3.65 (3H, s); 3.80 (3H, 2s); 5.10 (1H, 2s); 7.36 (1H, 2t); 7.65 (1H, t), 7.96 (1H, m); 8.13 (1H, 2s).

EXAMPLE 5

Preparation of methyl 2-methyl-4-(3-nitrophenyl)5-oxo-6-(2-(2-hydoxy-3-(2-methoxyphenoxy)-propylamino)-2-methylpropyl)-aminoethyl)-1,4,5,6,7,8-hexahydro-pyrido(3,4-b)pyridine-3-carboxylate Operating in a way similar to that disclosed in example 2 but using, as starting material, methyl 1,4-dihydro-6-methyl-2-(N-(2-(2-hydroxy-3-(2-methoxyphenoxy)-propylamino)-2-methylpropyl)-aminoethyl)-4-(3-nitrophenyl)-3,5-pyridinedicarboxylate prepared as disclosed in example 4, methyl 2-methyl-4-(3-nitrophenyl)-5-oxo-6-(2-(2-hydroxy-3-(2-methoxyphenoxy)-propylamino)-2-methylpropyl)-1,4,5,6,7,8-hexahydro-pyrido(3,4)pyridine-3-carboxylate is obtained.

$^1$H-NMR (300 MHz, CDCl$_3$): delta (ppm): 1.20 (6H, 4s); 2.40 (3H, d); 3.58 (3H, s); 3.80 (3H, s); 5.15 (1H, d); 7.32 (1H, t); 7.65 (1H, m); 7.92 (1H, dd); 8.06 (1H, m).

EXAMPLE 6

Preparation of ethyl 2-methyl-4-(3-nitrophenyl)-5-oxo-6-(2-amino-2-methyl-propyl)-1,4,5,6-tetrahydro-pyrido(2,3-d) pyridazine-3-carboxylate 2,2-dimethylaziridine (23 g; 0.32 moles) is added to hydrazine hydrate (82 ml); 1.64 mmoles) in two hours at 90° C. and under nitrogen atmosphere.

The mixture is heated at 120° C. for two hours.

The excess of hydrazine and then N-(2-methyl-2-aminopropyl-hydrazine (b.p. 76°-78° C./10 mmHg) are distilled under vacuum.

A mixture of N-(2-methyl-2-aminopropyl)-hydrazine (27 g; 0.26 moles) and of ethyl 1,4-dihydro-2-formyl-6-methyl-4-(3-nitrophenyl)-3,5-pyridinedicarboxylate (100 g; 0.26 moles) in n.butanol (1 L) is then heated to reflux for 30 hours.

After evaporation of the solvent, the crude product is purified by chromatography on silica gel column (230–400 mesh) eluting with a mixture of methylene chloride:ethanol 9:1.

Ethyl 2-methyl-4-(3-nitrophenyl)-5-oxo-6-(2-amino-2-methylpropyl)-1,4,5,6-tetrahydro-pyrido(2,3-d)pyridazine-3-carboxylate is obtained as a chromatographically pure oil (thin layer chromatography; eluent, methylene chloride:methanol:NH$_4$OH=86: 10:0.6).

$^1$H-NMR (300 MHz, CDCl$_3$): delta (ppm): 1.15 (9H, m); 2.45 (3H, s); 3.75 (1H, d); 4.05 (2H, q); 4.25 (1H, d);

5.35 (1H, s); 7.40 (1H, t); 7.60 (1H, s); 7.78 (1H, d); 8.00 (1H, d); 8.12 (1H, bs).

The following compound has been prepared in a similar way: ethyl 2-methyl-4-(3-nitrophenyl)-5-oxo-6-(2-aminoethyl)-1,4,5,6-tetrahydro-pyrido(2,3-d)pyridazine-3-carboxylate, chromatographically pure oil (thin layer chromatography; eluent, methylene chloride:methanol::NH$_4$OH=86:10:0.6).

$^1$H-NMR (300 MHz, CDCl$_3$): delta (ppm): 1.20 (3H,t); 2.43 (3H, s); 3.08 (2H, m); 3.95 (1H, m); 4.05 (2H, q); 4.28 (1H, m); 5.30 (1H, s); 7.40 (1H, t); 7.53 (1H, s); 7.75 (1H, d); 8.00 (1H, d); 8.12 (1H, bs).

EXAMPLE 7

Preparation of ethyl 2-methyl-4-(3-nitrophenyl)-5oxo-6-(2-(2-hydroxy-3-(2-methoxyphenoxy)-propylamino)-2-methylpropyl)-1,4,5,6,-tetrahydro-pyrido(2,3-d)pyridazine-3-carboxylate A solution of ethyl 2-methyl-4-(3-nitrophenyl)-5-oxo-6-(2-amino-2-methylpropyl)-1,4,5,6-tetrahydro-pyrido(2,3-d)pyridazine-3-carboxylate (2.0 g; 4.7 mmoles), prepared as described in example 6, and of 1,2-epoxy-3-(2-methoxyphenoxy)-propane (0.85 g; 4.7 mmoles) in 99% ethanol (20 ml) is heated to reflux for 3 hours.

The solvent is evaporated and the crude product is purified by chromatography on a silica gel column (230–400 mesh; eluent, methylene chloride:ethanol=95:5).

Ethyl 2-methyl-4-(3-nitrophenyl)-5-oxo-6-(2-(2-hydroxy-3-(2-methoxyphenoxy)-propylamino)-2-methylpropyl)-1,4,5,6-tetrahydro-pyrido(2,3-d)pyridazine-3-carboxylate is obtained as a chromatographically pure oil (thin layer chromatography; eluent, methylene chloride:methanol:NH$_4$OH=86:10:0.6).

$^1$H-NMR (300 MHz, DMSO-D ): delta (ppm): 1.10 (9H, m); 2.50 (3H, s); 3.78 (3H, 2s); 3.85 (1H, 2d); 4.28 (1H, 2d); 5.12 (1H, d); 7.38 (1H, t); 7.45 (1H, 2s); 7.78 (1H, d); 8.00 (1H, d); 8.12 (1H, bs).

The following compound has been prepared in a similar way: ethyl 2-methyl-4-(3-nitrophenyl)-5-oxo-6-(2-(2-hydroxy-3-(2-methoxyphenoxy)-propylamino)-ethyl)-1,4,5,6-tetrahydropyrido(2,3-d)pyridazine-3-carboxylate.

$^1$H-NMR (300 MHz, DMSO-d$_6$) delta (ppm): 1.10 (3H, t); 2.40 (3H, s); 3.74 (3H, 2s); 4.45 (1H, m); 5.18 (1H, d); 7.55 (1H, t); 7.68 (1H, d); 7.80 (1H, bs); 8.05 (1H, d); 8.07 (1H, bs).

EXAMPLE 8

Preparation of methyl 6-(2-phthalimidoethyl)2-methyl-4-(3-nitrophenyl)-5-oxo-1,4,5,6tetrahydro-pyrido(2,3-d)pyridine-3-carboxylate A mixture of methyl 2-methyl-4-(3-nitrophenyl)-5-oxo-1,4,5,6-tetrahydro-pyrido(2,3-d)pyridine-3-carboxylate (2 g; 5.8 mmoles), N-(2-iodoethyl)-phthalimide (2 g; 6.6 mmoles) and potassium carbonate (2 g; 14.4 mmoles) in dioxane (40 ml) is heated to reflux for 15 hours.

After evaporation of the solvent, the crude product is purified by chromatography on a silica gel column (230–400 mesh) eluting with a mixture of methylene chloride and ethanol 95:5.

Methyl 6-(2-phthalimidoethyl)-2-methyl-4-(3-nitrophenyl)-5-oxo-1,4,5,6-tetrahydro-pyrido(2,3-d)pyridine-3-carboxylate is obtained as a chromatographically pure amorphous solid (thin layer chromatography; eluent, methylene chloride:methanol:NH$_4$OH=94.5:5:0.5).

$^1$H-NMR (300 MHz, DMSO-d$_6$) delta (ppm): 2.35 (3H, s); 3.50 (3H, s); 3.80 (2H, m); 4.00 (2H, t); 5.00 (1H, s); 5.90 (1H, d); 7.40 (1H, d); 7.42 (1H, t); 7.55 (1H, d).

EXAMPLE 9

Preparation of methyl 6-(2-phthalimidoethyl)2-methyl-4-(3-nitrophenyl)-5-oxo-1,4,5,6-tetrahydro-pyrido(2,3-d)pyrimidine-3-carboxylate A solution of methyl 2-methyl-4-(3-nitrophenyl)-5-oxo-1,4,5,6-tetrahydro-pyrido(2,3-d)pyrimidine-3-carboxylate (2 g; 5.8 mmoles) in dimethylformamide (50 ml) is added to a 55% suspension of sodium hydride in paraffin oil (0.27 g; 6.2 mmoles) in anhydrous dimethylformamide under stirring and nitrogen atmosphere.

The mixture is reacted under the same conditions for 30 minutes and is then treated with a solution of N-(2-iodoethyl)-phthalimide (0.17 g; 5.8 mmoles) in dimethylformamide (50 ml) for 2 days at room temperature.

The mixture is extracted with water and ethyl acetate, the organic phase is separated and dried over sodium sulfate.

After evaporation of the solvent, the residue is purified by chromatography on a silica gel column (70–230 mesh) eluting with methylene chloride:ethyl acetate=3:7.

Methyl 6-(2-phthalimidoethyl)-2-methyl-4-(3-nitrophenyl)-5-oxo-1,4,5,6-tetrahydro-pyrido(2,3-d)pyrimidine-3-carboxylate is obtained.

$^1$H-NMR (300 MHz, DMSO-d$_6$) delta (ppm): 2.38 (3H, s); 3.50 (3H, s); 3.84 (2H, m); 4.04 (2H, m); 5.02 (1H, s); 8.28 (1H, s).

EXAMPLE 10

Preparation of methyl 6-(2-aminoethyl)2-methyl-4-(3-nitrophenyl)-5-oxo-1,4,5,6-tetrahydro-pyrido(2,3-d)pyridine-3-carboxylate A solution of methyl 6-(2-phthalimidoethyl)-2-methyl-4-(3-nitrophenyl)-5-oxo-1,4,5,6-tetrahydro-pyrido(2,3-d)pyridine-3-carboxylate (2 g; 3.9 mmoles), prepared as described in example 8, in dimethylformamide (5 ml) is treated with a 33% solution of methylamine in ethanol (28 ml) under stirring and at room temperature for two days.

After evaporation of the solvent, the crude product is extracted with water and methylene chloride. The organic phase is separated and dried over sodium sulfate. The residue obtained after evaporation of the solvent is purified by chromatography on a silica gel column (230–400 mesh) eluting with a mixture of methylene chloride and of increasing quantities of ethanol from a ratio of 95:5 to a ratio of 85:15.

Methyl 6-(2-aminoethyl)-2-methyl-4-(3-nitrophenyl)-5-oxo-1,4,5,6-tetrahydro-pyrido(2,3-d)pyridine-3-carboxylate is separated as a chromatographically pure oil (thin layer chromatography; eluent, methylene chloride:methanol:NH$_4$OH=86:10:0.6).

$^1$H-NMR (300 MHz, DMSO-d$_6$): delta (ppm): 2.4 (3H, s); 2.7 (2H, m); 5.3 (1H, s); 6.2 (1H, d).

Operating in a similar way the following compound has been prepared: Methyl 6-(2-aminoethyl)-2-methyl-4-(3-nitrophenyl-5-oxo-1,4,5,6-tetrahydro-pyrido(2,3-d)pyrimidine-3-carboxylate 1H-NMR (300 MHz, DMSO-d$_6$): delta (ppm): 2.40 (3H, s); 2.70 (2H, t); 3.52 (3H, s); 3.61 (1H, m); 3.72 (1H, m); 5.16 (1H, s); 8.18 (1H, s).

EXAMPLE 11

Preparation of methyl 2-methyl-6-(2-(2-hydroxy-3-(2-methoxyphenoxy)-propylamino)-ethyl)-4-(3-nitrophenyl)-5-oxo-1,4,5,6-tetrahydropryrido-(2,3-d)pyridine-3-carboxylate A solution of methyl 6-(2-aminoethyl)-2-methyl-4-(3-nitrophenyl)-5-oxo-1,4,5,6-tetrahydropyrido(2,3-d)pyridine-3-carboxylate (1.6 g; 4.16 mmoles), prepared as described in example 10, and of 1,2-epoxy-3-(2-methoxyphenoxy)-propane (0.83 g; 4.16 mmoles), in acetonitrile (112 ml) is heated to reflux for 8 hours under an inert atmosphere.

After evaporation of the solvent and purification of the crude product by chromatography on a silica gel column (230–400 mesh; eluent, methylene chloride:ethanol=95:5), methyl 2-methyl-6-(2-(2-hydroxy-3-(2-methoxyphenoxy)-propylamino)-ethyl)-4-(3-nitrophenyl)-5-oxo-1,4,5,6-tetrahydropyrido-(2,3-d)pyridine-3-carboxylate is obtained, which is then salified with hydrochloric acid, by treatment with a solution of HCl in ethyl ether and filtration of the separated solid.

1H-NMR (free base) (300 MHz, CDCl$_3$): delta (ppm): 2.42 (3H, s); 3.60 (3H, s); 3.80 (3H, s), 5.30 (1H, d); 5.85 (1H, d); 7.18 (1H, dd); 7.35 (1H, t); 7.77 (1H, d); 7.94 (1H, dd); 8.11 (1H, bs).

Operating in a similar way the following compound has been prepared: Methyl 2-methyl-6-(2-(2-hydroxy-3-(2-methoxyphenoxy)-propylamino)-ethyl)-4-(3nitrophenyl)-5-oxo-1,4,5,6-tetrahydropyrido(2,3-d)pyrimidine-3-carboxylate 1H-NMR (300 MHz, CDCl$_3$): delta (ppm): 2.45 (3H, s); 2.80 (2H, m); 2.95 (2H, m); 3.60 (3H, s); 3.80 (3H, s); 5.30 (1H, s); 7.38 (1H, t); 7.74 (1H, d); 7.96 (1H, s); 7.98 (1H, d); 8.13 (1H, bs).

EXAMPLE 12

Investigation on the Pharmacological Activity

Calcium antagonist activity of the compounds of formula I has been tested as capability of antagonizing the effect of Ca$^{++}$ submaximal concentrations (3 mM) on preparations of rabbit mesenteric artery in Krebs depolarizer, prepared according to Towart "J. Cardiovasc. Pharmacol." 4, 895, (1982).

Moreover the beta-blocking activity has been tested with i binding tests both towards beta$_1$ heart receptors and beta$_2$ lung receptors in mouse according to methods described in J. Biol. Chem., 253, 5090, (1978) and Br. J. Pharmacol., 68, 57, (1980).

The compounds of formula I proved to have more affinity towards beta$_1$ receptors than towards beta$_2$ receptors.

The compounds of formula I, tested as calcium antagonist agents on the rabbit mesenteric artery, show an IC$_{50}$ of from 0.20 to 5 (uM); Ki affinity for beta$_1$ receptors is of from 600 to 3500 (nM) and for beta$_2$ is of from 700 to 3000 (nM).

By way of example, IC$_{50}$ (uM) and receptorial affinity data as Ki (nM) are given in the following table 1 for the following compounds of formula I:

Compound A

Ethyl 2-methyl-4-(3-nitrophenyl)-5-oxo-6-(2-(2-hydroxy-3-(2-methoxyphenoxy)-propylamino)-ethyl)-1,4,5,6-tetrahydro-pyrido(2,3 -d)pyridaxine-3-carboxylate Compound B Ethyl 2-methyl-(4-(3-nitrophenyl)-5-oxo-6-(2-(2-hydroxy-3-(2-methoxyphenoxy)-propylamino)-2-methylpropyl)-1,4,5,6-tetrahydro pyrido(2,3-d)pyridazine-3-carboxylate.

TABLE 1

| | IC$_{50}$ (uM) and receptorial affinity Ki (nM) of compound A and B. | | |
|---|---|---|---|
| COMPOUND | IC$_{50}$ (uM) rabbit mesenteric artery | Ki (nM) mouse heart beta$_1$ receptors | Ki (nM) mouse lung beta$_2$ receptors |
| A | 0.24 | 345 | 287 |
| B | 0.77 | 142 | 71 |

We claim:

1. A pharmacologically-acceptable compound of the formula:

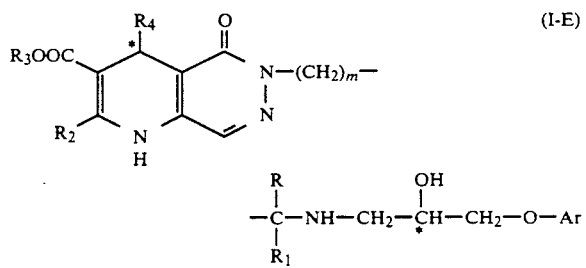

wherein Ar is a member selected from the group consisting of 2-methoxyphenyl, 2-allyloxyphenyl, 2-cyanophenyl, 2-methylphenyl, 2-allylphenyl, carbamoylmethylphenyl, 4-hydroxyphenyl, 4-morpholino-1,2,5-thiadiazol-3-yl, indol-4-yl and 3,4-dihydro- 1(H)-carbostyrl-5-yl;

each of R and R$_1$ is, independently, hydrogen or methyl, R$_2$ is methyl, R$_3$ is methyl, ethyl or isopropyl; R$_4$ is optionally-substituted phenyl any substituent of which is a member selected from the group consisting of halogen, hydroxy, C$_1$–C$_5$ alkyl, C$_2$–C$_5$ alkenyl, C$_1$–C$_3$ alkoxy, C$_2$–C$_5$ alkenyloxy, alkoxyalkyl having from 1 to 5 carbon atoms both in the alkyl and alkoxy moiety, C$_2$–C$_5$ alkanoyl, trifluoromethyl, amino, nitro, carbamoyl, cyano, C$_1$–C$_3$ alkylthio, carbamoyl (C$_1$–C$_6$) alkyl and C$_1$–C$_6$ alkanoylamino, m is 1; and the asterisks denote asymmetric carbon atoms; or a salt thereof with a pharmaceutically-acceptable organic or inorganic acid.

2. A pharmaceutical composition containing an effective amount of a compound of formula I or a pharmaceutically-acceptable salt thereof as defined in claim 1 together with one or more solid or liquid, organic or inorganic pharmaceutical excipients.

3. A pharmaceutical composition useful for treating cardiovascular pathologies and comprising, per unit dose, from 0.1 to 200 mg of a compound according to claim 1 or of a pharmacologically-acceptable salt thereof and pharmaceutical excipient.

4. A method of treating a patient afflicted with cardiovascular pathology which comprises administering to the patient an effective amount of a compound according to claim 1 or of a pharmacologically-acceptable salt thereof.

* * * * *